United States Patent [19]

Sell et al.

[11] Patent Number: 5,069,061
[45] Date of Patent: Dec. 3, 1991

[54] ESTIMATION OF FUMIGANT RESIDUES IN COMMODITIES

[75] Inventors: Charles R. Sell; Mark A. Weiss, both of Yakima, Wash.

[73] Assignee: The United States of America as represented by the Secretary of Agriculture, Washington, D.C.

[21] Appl. No.: 459,405

[22] Filed: Dec. 29, 1989

[51] Int. Cl.$^5$ .............................................. G01N 7/00
[52] U.S. Cl. ..................................... 73/19.01; 425/320
[58] Field of Search ........................... 73/19.01, 31.02; 426/319, 320

[56] References Cited

U.S. PATENT DOCUMENTS 4,812,291 3/1989 Friemel et al. ................. 42.6/320 X

OTHER PUBLICATIONS

C. R. Sell, N. G. Klag, and A. K. Burditt, "Methyl Bromide Residues in Fresh Cherries: Effects of Parameters of Fumigation", *Pesticide Science*, 23: 41-49 (1988).

*Primary Examiner*—Jerry W. Myracle
*Attorney, Agent, or Firm*—M. Howard Silverstein; John D. Fado; Margaret A. Connor

[57] ABSTRACT

A method and apparatus are described for accurately estimating the concentration of residual fumigant in a commodity in a fumigation chamber from the rate of decline in concentration of fumigant in the exhaust air stream during the aeration period following fumigation. Because the method is nondestructive and lends itself to automation, it us useful for commercial application.

8 Claims, 4 Drawing Sheets

ESTIMATION OF FUMIGANT RESIDUES IN COMMODITIES

BACKGROUND OF THE INVENTION

1. Field of the Invention

This invention relates to a method and apparatus for accurately estimating the concentration of residual fumigant in a commodity in a fumigation chamber from the decline in concentration of fumigant in the exhaust air stream during the aeration period following fumigation.

2. Description of the Art

Gaseous fumigants are important for the commercial control of pests in a variety of commodities. Methyl bromide (MB) is a highly toxic, colorless, odorless gas that is widely used as a fumigant for fresh fruit and other agricultural products. This highly penetrating gas can kill insects and other arthropod pests within the commodities. When the commodities are treated with MB, a small portion of the gas reacts with the product producing relatively innocuous inorganic bromide residue, and the remaining MB desorbs from the product. Free MB, however, can persist in commodities for some time after fumigation, and exposure through inhalation and ingestion may be hazardous to workers that handle fumigated commodities and to the consumer. MB residues have become a concern of the United States Environmental Protection Agency (EPA), and residue data for a large number of agricultural products is required to support continued use of this important fumigant.

In the Pacific Northwest a treatment using MB as a fumigant is being developed for apples to satisfy import quarantine requirements for Japan and other countries. Fumigation would be followed by an aeration period in which fresh air is forced through the fumigation chamber to remove gaseous MB from the free air space. Animal Plant Health Inspection Service (APHIS) guidelines require that aeration must continue until the concentration of MB in the exhaust air stream evacuated from the chamber is 5 parts per million (ppm) or less. This requirement is intended to protect workers who enter the chamber immediately after the aeration period and is not concerned with residues of MB in the commodity. As a result of this requirement, the length of the aeration period is determined by the ventilation rate, because higher ventilation rates more effectively dilute the MB in the exhaust air stream and as a result shorten the aeration periods. Present regulations do not specify a tolerance for free MB in apples, although a tolerance of 0.2 ppm has been proposed (EPA, *Federal Register* 51: 9512 (1986)). Previous work on residues of free MB in sweet cherries has shown that the aeration periods commonly used in commercial fumigations are usually too short to reduce MB to below 1 ppm (Sell et al., *Pesticide Science* 23: 41-49 (1988)). It is highly desirable to remove MB residues from commodities during the aeration period, before there is human contact with the treated commodity. Presently, the way to *precisely* determine MB residue concentrations in fumigated commodities is the headspace analysis method. This is a destruction method wherein a sample of the commodity is homogenized in water, and the headspace (gaseous phase above the homogenate) is assayed using gas chromatography. (See King et al., *Journal of Agricultural and Food Chemistry* 29: 1003-1005 (1981)). While useful for laboratory studies where experiments can be carried out in a fume hood, headspace analysis cannot be used to determine residue concentration during aeration in a commercial fumigation chamber because the chamber would have to be entered to remove the sample for analysis. This would be highly hazardous to workers.

Another commercially important fumigant for control of pests in a variety of commodities is ethylene dibromide (1,2-dibromoethane, EDB). Although EDB has been removed from the U.S. market, it is still used as a fumigant in other markets in the world. As with MB, precise determination of EDB residues requires destructive testing that can result in exposure of the workers to the gas. What is needed is a method for determining fumigant residue concentrations in treated commodities which is nondestructive, minimizes exposure of workers to the fumigant, and is suitable for commercial use.

SUMMARY OF THE INVENTION

We have discovered a novel system for accurately estimating the concentration of residual fumigant in a commodity in a fumigation chamber from a predetermined relationship of selected determinants including the rate of decline in concentration of fumigant in the exit gas (exhaust air stream) during the aeration period following fumigation. Our system provides a method for reducing residual fumigant to a desirable level in a commodity in a fumigation chamber. Because our system is nondestructive and lends itself to automation, it is useful for commercial application.

The method of the invention for reducing residual fumigant to a desirable level in a commodity in a fumigation chamber having a free air space therein, comprises:

(a) determining the weight of the commodity in the chamber;

(b) passing a gas through the chamber in first and second phases to remove fumigant; wherein the free air space is depleted of fumigant and fumigant is released from the commodity during the first phase; wherein fumigant in the commodity is further released therefrom during the second phase; wherein the gas is passed through the chamber during the second phase at a known volumetric flow rate;

(c) determining the rate of decline of fumigant in gas exiting from the chamber during the second phase, so that there is a continual or intermittent update of the rate of decline;

(d) determining the concentration of fumigant in gas exiting from the chamber at the beginning of the first phase that is due to fumigant released from the commodity;

(e) continuing the second phase at least until the desirable level of residual fumigant in the commodity is reached as estimated from a predetermined relationship between:

(i) the weight,
  (ii) the volumetric flow rate,
  (iii) the concentration of fumigant in exit gas at the beginning of the first phase that is due to fumigant released from the commodity;
  (iv) the latest update of the rate of decline of fumigant in exit gas;
  (v) the length of time between the beginning of the first phase and the latest update of the rate of decline.

The apparatus of the invention which is operatively associated with a fumigation chamber, provides a means for carrying out the above method. In brief, the apparatus comprises:

(a) means communicating with the exhaust stack of a fumigation chamber for sampling the gas exiting the chamber and for transferring the exit gas sample to a fumigant analyzer;

(b) a fumigant analyzer communicating with the sampler means which produces a signal in response to concentration of fumigant in the exit gas sample, and (c) computing means operatively associated with the fumigant analyzer for computing the level of residual fumigant in the commodity as estimated from a predetermined relationship as described above.

In accordance with this discovery, it is an objective of the invention to provide a system for reducing residual fumigant in a commodity which is fumigated in a fumigation chamber to a desirable level.

It is a further object of the invention to provide a method and apparatus for accurately estimating the concentration of residual fumigant in a commodity during the aeration period following fumigation from the decline in concentration of fumigant in the exhaust gas air stream. The invention provides a noninvasive and nondestructive method for estimating residue concentration, because the fumigation chamber does not have to be entered and the fumigated commodity does not have to be handled and destroyed during testing.

It is also an object of the invention to provide a nondestructive method for estimating fumigant residues in commodities which is suitable for commercial use.

Another object of the invention is to provide a means to monitor fumigant residues while minimizing exposure of workers to the fumigant.

The invention finds particular use in the estimation of fumigant residues in agricultural commodities.

Other objects and advantages of the invention will become readily apparent from the ensuing description.

DETAILED DESCRIPTION OF THE INVENTION

Gaseous fumigants are used worldwide for the commercial control of pests in a variety of commodities, for example, dried and fresh fruit, vegetables, nuts, grain, crops, cocoa beans, coffee beans, tobacco, candy, cereals, cheese, dried eggs, flour, herbs and seasonings or spices, meat products, dog-feed, ornamentals, and the like. Examples of fumigants include methyl bromide, ethylene dibromide, hydrogen cyanide, phosgene, ethylene oxide, and the like. Fumigants are highly toxic and penetrating gases that are capable of killing insects inside of commodities. Fumigation is carried out by exposing the commodity to a fumigant for a prescribed length of time (in the U.S., this is generally set by APHIS) in a hermetically sealed chamber. The fumigation is followed by an aeration period where a gas is forced through the fumigation chamber to remove the fumigant from the chamber.

The present invention provides a system for reducing residual fumigant in a commodity which is fumigated in a fumigation chamber to a desirable level. In the method of the invention, gas is passed through the fumigation chamber in first and second phases during the aeration period following fumigation to remove fumigant from a fumigated commodity having a determined weight. In the first phase, fumigant is depleted from the free air space in the fumigation chamber and fumigant is released from the commodity. In the second phase, fumigant in the commodity is further released therefrom. The gas is passed through the fumigation chamber during the second phase at a known volumetric flow rate (ventilation rate of exhaust gas through the fumigation chamber). The rate of decline of fumigant in the exhaust gas exiting from the chamber during the second phase is determined to obtain a continual or intermittent update of the rate of decline of fumigant. The concentration of fumigant in gas exiting from the chamber at the beginning of the first phase that is due to fumigant released from the commodity is determined. The second phase is continued at least until the desirable level of residual fumigant in the commodity is reached as estimated from a predetermined relationship between the weight of the commodity in the chamber, the volumetric flow rate of the gas during the second phase, the concentration of fumigant in exit gas at the beginning of the first phase that is due to fumigant released from the commodity, the latest update of the rate of decline of fumigant in the exit gas, and the length of time between the beginning of the first phase and the latest update of rate of decline.

Figure 2:
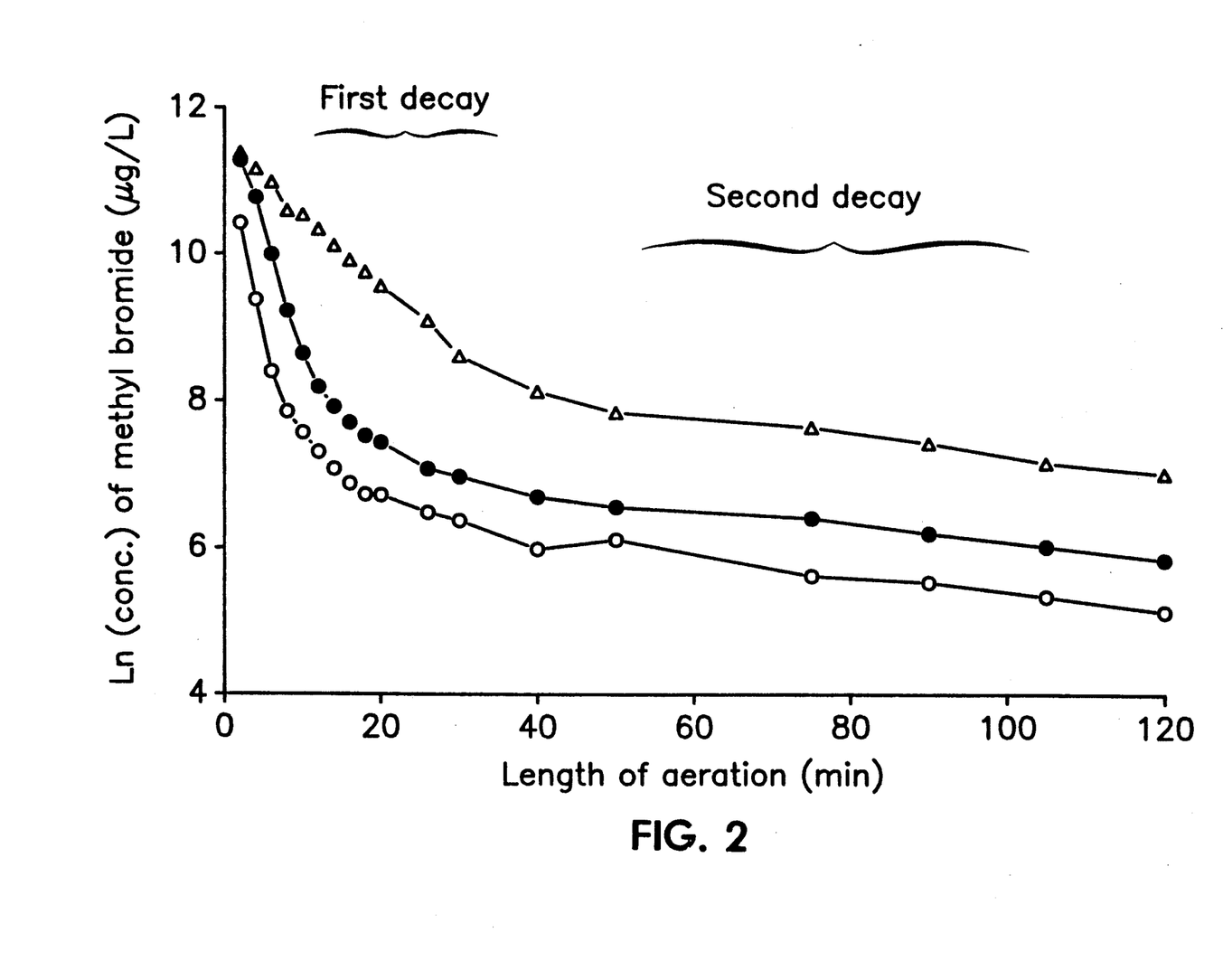
FIG. 2 illustrates the effect of ventilation rate on the concentration of methyl bromide in the exhaust air stream from fumigated apples. Ventilation rates were (△) 5.3 changes/h, (•) 14.1 changes/h, and (○) 20.6 changes/h. The load factor (ratio of the volume of the commodity to the volume of the fumigation chamber expressed as a percentage) and temperature of the fruit for the fumigations were 18% and 16° C., respectively.
Figure 4:
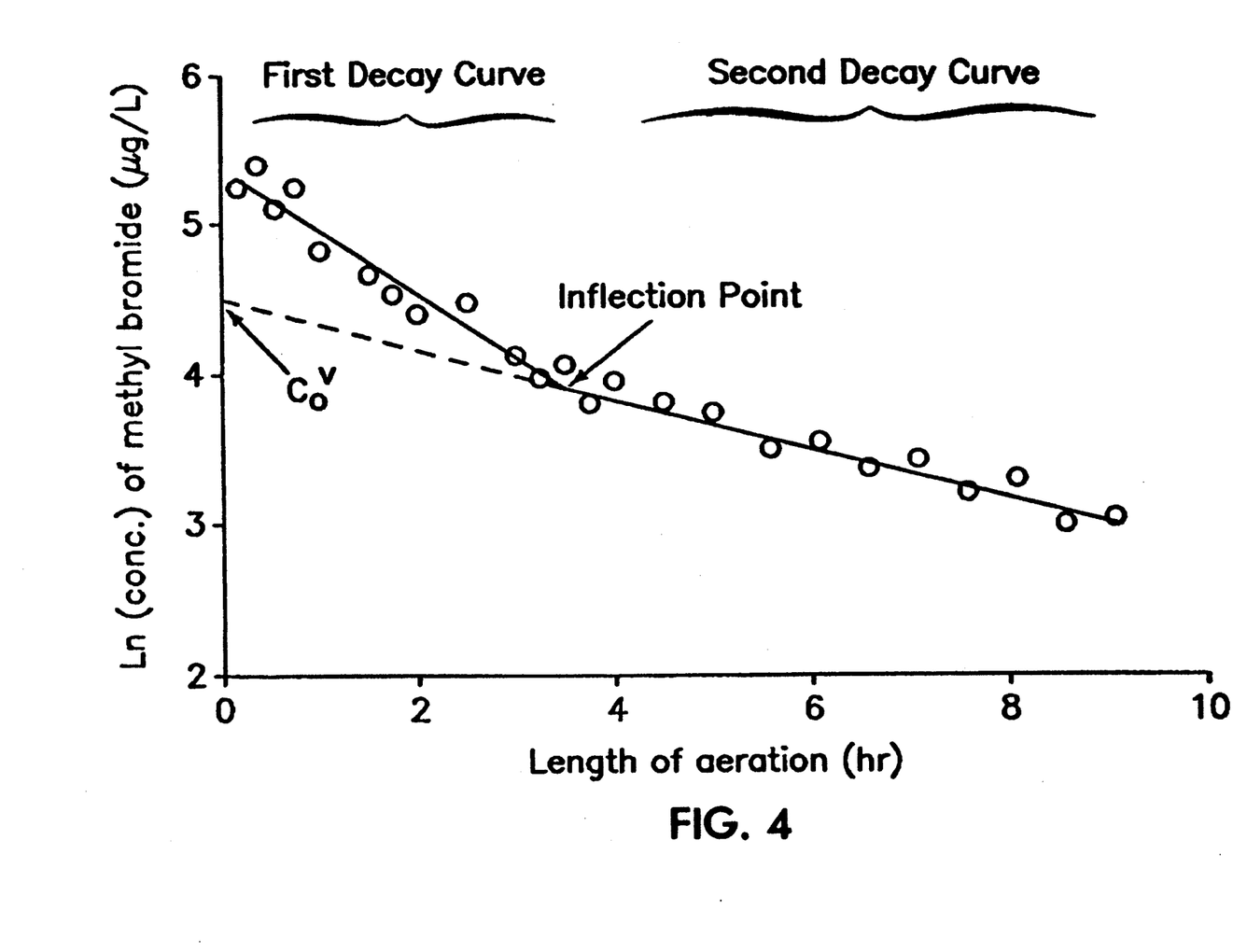
FIG. 4 shows the rate of decline of methyl bromide concentration in the exhaust air stream from fumigated walnuts during the aeration period following fumigation.

The present invention also provides a method for accurately estimating the concentration of residual fumigant in a commodity during the aeration period, using a prediction equation. The method involves determining the rate of decline in the concentration of fumigant in the exit gas (exhaust air stream) from a fumigation chamber during the aeration period following fumigation. The rate of decline follows two consecutive pseudo-first-order decay curves as illustrated in FIGS. 2 and 4. The first decay curve results primarily from removing fumigant from the free air space in the chamber and to a lesser extent from release of fumigant from the commodity and is unrelated to concentration of residual fumigant. [This is denoted as the first phase.] The second decay curve results from the further slow release of fumigant from the commodity (second phase). Onset of the second decay curve is indicated by a change in slope which indicates that the first decay curve has been completed and the second decay curve has begun. The point of inflection, which is the transition point between the two decay curves, is determined mathematically by techniques known in the art, e.g., piecewise linear regression, cubic interpolatory spline method and the like. After the second decay curve has begun, the concentration of residual fumigant in the commodity is estimated from the prediction equation:

$$C = (QC_o^v/Wk^v) \exp(-k^v t)$$

wherein C is the concentration of residual fumigant in the commodity at time t after the beginning of the first phase of aeration; Q is the volumetric flow rate (ventilation rate of the exhaust air stream through the fumigation chamber) during the second phase; $C_o^v$ is the concentration of fumigant in the gas exiting the fumigation chamber at the beginning of the first phase, i.e., beginning of aeration, that is due to the fumigant released from the commodity; W is the weight of the commodity in the fumigation chamber, and $k^v$ is the rate of decline of fumigant in gas exiting from the chamber during the second phase (slope of the second decay curve). $C_o^v$ (the amount of fumigant in the exit gas due to fumigant released from the commodity at the beginning of aeration) is obtained by extrapolation of the second decay curve to time zero, e.g., by taking the antilog of the y-intercept of the second decay curve as shown in FIG. 4. $C_o^v$ can be determined graphically or mathematically by techniques known in the art, for example, linear regression. Charts, tables, and graphs based upon the above prediction equation may be employed in lieu of calculations.

To use the prediction equation, the volumetric flow rate of the exhaust air stream through the chamber at least during the second phase is a known value Q.

A procedure for performing a fumigation and estimating the concentration of residual fumigant in a commodity in accordance with the method of the invention is carried out as follows:

(1) The weight of the commodity (constant W in the prediction equation) is determined.

(2) The commodity is placed in the fumigation chamber, and the chamber is hermetically sealed.

(3) The fumigant is injected into the chamber, and the commodity is exposed to the fumigant for the prescribed length of time.

(4) The air intake ports in the chamber are opened and the exhaust fans are turned on, thereby beginning the aeration period.

(5) The exhaust air stream is sampled after aeration begins.

(6) The sample of step (5) is analyzed to determine the concentration of fumigant in the exhaust air stream.

(7) Steps (5) and (6) are repeated to determine the rate of decline of fumigant in the exhaust air stream during the aeration period. The point of inflection which indicates that the second decay curve has begun is determined by known methods as described above.

(8) Steps (5) and (6) are repeated to determine the rate of decline of fumigant in the exhaust air stream during the second decay curve ($k^v$ in the prediction equation).

(9) The concentration of fumigant in the exhaust air stream at the beginning of aeration that is due to the fumigant released from the commodity ($C_o^v$ in the prediction equation) is determined as described above.

(10) The concentration of residual fumigant in the fumigated commodity is estimated using the prediction equation:

$$C = (QC_o^v/Wk^v) \exp(-k^v t).$$

(11) Steps (8), (9), and (10) are repeated until the estimated concentration of residual fumigant in the commodity is reduced to the desired concentration.

(12) The fumigated commodity is removed from the fumigation chamber.

The prediction equation is useful to accurately estimate the concentration of residual fumigant in any commodity provided desorption of fumigant from the commodity follows pseudo-first-order kinetics. That is, the rate of decline in concentration of residual fumigant depends on concentration of fumigant remaining in the commodity. Published scientific information indicates that desorption of fumigant from commodities follows pseudo-first-order kinetics. In those cases where published information about the kinetics of desorption is not available, it can be readily determined for a commodity by routine experimentation as shown in Example 1 below. Commodities that are known to follow first-order-kinetics include fresh fruits such as apples, cherries, and citrus, and nuts.

The prediction equation is useful over a wide range of fumigation conditions. As shown in Example 1 below, the technique is accurate over a range of load factors (ratio of volume of the commodity to the volume of the fumigation chamber expressed as a percentage), commodity temperatures, and ventilation rates.

The method can also be used to calculate the time t to reach the desired tolerance of fumigant residue in the commodity. Assuming that the commodity must be aerated until the concentration of fumigant residue in the commodity reaches a tolerance of $C_t$, then the length of the aeration required to achieve this tolerance is obtained by rearrangement of the prediction equation giving:

$$t = (1/k^v) \ln (QC_o^v/Wk^v C_t).$$

Parameters of the second day curve can be used to obtain a qualitative estimate of residual fumigant remaining in a commodity. A qualititative esimate of the persistence of the residue is obtained by calculating a half-life of the residue from the equation:

$$t_{\frac{1}{2}} = (\ln 2)/k^v$$

where $t_{\frac{1}{2}}$ is the half-life, ln 2 is the natural log of 2, and $k^v$ is the slope of the second decay curve.

Applicability of the method for accurately estimating fumigant residues in commodities is illustrated in the examples below.

Figure 1:
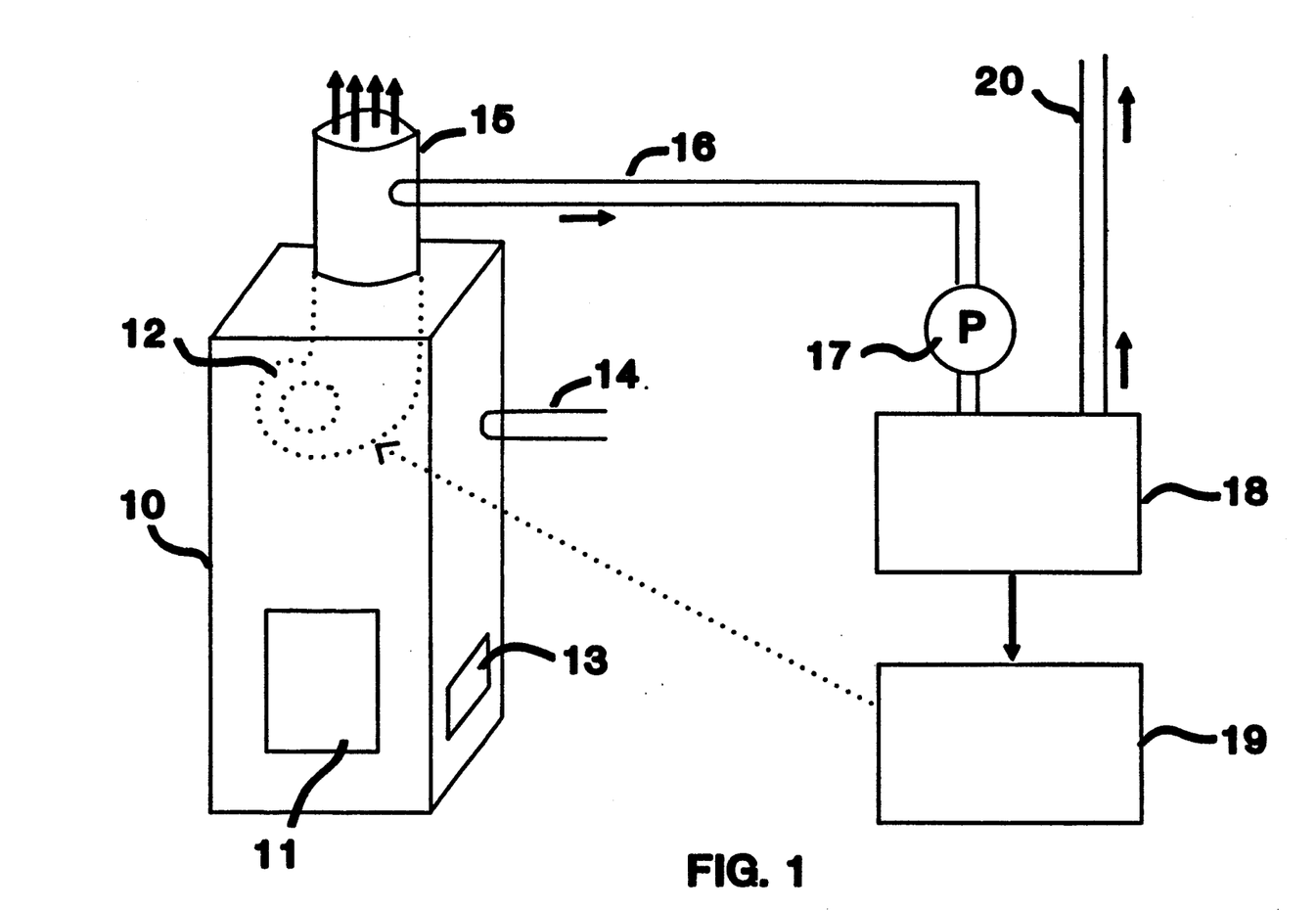
FIG. 1 is a simplified schematic drawing illustrating the apparatus of the invention.

An apparatus for carrying out the method to reduce residual fumigant to a desirable level in a commodity or to accurately estimate the concentration of residual fumigant in a commodity is shown in FIG. 1. The apparatus is operatively associated with a fumigation chamber (10 in FIG. 1). A variety of materials, shapes, and sizes are possible for construction of the chamber. The chamber has door 11 for loading and removing a commodity, fan 12 for circulating the fumigant during fumigation and venting the fumigant during aeration, air intake port 13 that can be opened to allow air to enter the chamber during aeration, and gas injection port 14 for injecting gaseous fumigant. The chamber must be capable of being hermetically sealed. Attached to the fumigation chamber is exhaust stack 15. The exhaust stack is a conduit for removing exhaust air stream from the fumigation chamber during aeration. The stack is generally constructed of sheet metal, and is usually attached to the wall or roof of the chamber. The exhaust gas which is composed of a mixture of air and fumigant is exhausted through the exhaust stack during the aeration period following fumigation.

The apparatus of the invention includes means communicating with the exhaust stack of a fumigation chamber for sampling the exhaust gas exiting the chamber and for transferring the exit gas sample to a fumigant analyzer. This is shown in FIG. 1 as an exhaust air stream sampler (tubing 16) communicating with the exhaust stack of the fumigation chamber for sampling the exhaust gas venting from the exhaust stack and pump 17 for transferring the exit gas sample from the exhaust stack to a fumigant analyzer. Communicating with the sampler means is a fumigant analyzer (18) which produces a signal in response to concentration of fumigant in the exit gas sample. Computing means 19 is operatively associated with the fumigant analyzer for computing the level of residual fumigant in the commodity as estimated from a predetermined relationship as described above.

In practice, the exit gas is sampled by sampler 16, and the sample is transferred to fumigant analyzer 18 by pump 17. The signal produced by the fumigant analyzer in response to the concentration of fumigant in the sample is presented to computing means 19. The computing means computes the concentration of residual fumigant in the commodity from the predetermined relationship described above or computes the time required to achieve the desired fumigant tolerance as described above. In cases where the sample is not destroyed by the fumigant analyzer, it is transported via tube 20 out of the system. The sample can be returned to the exhaust stream.

The exit gas sampler and sample transfer means can be tubing and pump as shown in FIG. 1 or any functionally equivalent devices as known to those skilled in the art. The fumigant analyzer can be any device which determines the concentration of fumigant in the sample, that is, the device produces a signal in response to the concentration of fumigant in the sample. Examples of such devices include an infrared gas analyzer, a flame photometer, and a photoionization analyzer. Any computing means which is capable of computing residual fumigant concentration at time t after aeration begins using the predetermined relationship can be used. An efficient computing means is a computer. It may be an ancillary device or interfaced to the fumigant analyzer. The preferred computing means is a computer equipped with a time of day clock which is accessible to the operating program, and the circuitry necessary to convert an analog input voltage signal from the fumigant analyzer to a digital number with at least 6 bits of resolution. The computer can use any available programming language as long as the implemented program can access the time clock and analog input circuitry. Examples are the Epson PX-8 Geneva portable computer, the IBM PC with analog to digital input circuit board, Apple II or Macintosh computers with the appropriate time of day and analog to digital conversion circuitry. A computer program for computing the estimate of fumigant residue in a commodity from the decline of concentration of fumigant in the exhaust air stream using the prediction equation is presented in Example 4 below.

The invention can be automated. For example, the concentration of residual fumigant in a fumigant commodity can be monitored by successively estimating the residual fumigant using the prediction equation as discussed above, and then when C reaches a preset value, an alarm is sounded which indicates that the residual concentration in the commodity has reached the desired level. Similarly, the prediction equation which calculates the time t to reach the desired tolerance of fumigant residue in the commodity can be used. The commodity is aerated until the concentration of fumigant residue in the commodity reaches a tolerance of $C_t$. The computer can be programmed to sound an audible alarm which indicates that residue concentration in the commodity has dropped to the tolerance concentration, and that the commodity can be safely removed from the chamber. Or the computer means can be operatively associated with the fumigation chamber to discontinue the second phase when the desirable level of fumigant in the commodity is reached.

EXAMPLES

The following examples are intended only to further illustrate the invention and are not intended to limit the scope of the invention which is defined by the claims.

EXAMPLE 1

Experimental Methods

Fumigation Procedure. Immature apples, about 2 to 3 cm in diameter, obtained from trees at thinning, were fumigated using a 28.3 liter fiberglass vacuum desiccator as a fumigation chamber. The dessicator was pierced in opposite corners with 12.5 mm ID pipe that served as the air intake and exhaust ports, and a fan was installed inside to circulate air during the fumigation and during aeration. The fumigation chamber was placed in an environmental chamber (Percival Co., Boone, IA) for temperature control and the fumigations were repeated at various fruit pulp temperatures, load factors (i.e. ratio of the volume of apples to the volume of the fumigation chamber expressed as a percentage), and ventilation rates.

The average density was determined by weighing 30 apples in groups of 3 and determining the volume of each group by submersion in water. The density was then used to calculate load factor. Apples were placed in a wire-mesh basket, weighed, and transferred to the fumigation chamber at least three days before fumigation to allow pulp temperature to equilibrate with the temperature of the environmental chamber. Before fumigation, a slight vacuum was created in the chamber. Pure gaseous MB (375 ml), obtained from Matheson Co., East Rutherford, NJ, was injected by syringe into the chamber through a stopcock, and the vacuum was released. The concentration of MB was 56 $g/m^3$ for all fumigations. A fan inside the fumigation chamber circulated the air during the fumigation period and during the subsequent aeration period. After 2 hours of fumigation, intake and exhaust ports were opened, and air was drawn through the fumigation chamber.

Preliminary experiments determined the effect of ventilation rate on the rate of decline of MB in the exhaust air stream. A gas sampling bottle (125 ml) was placed in the exhaust line to collect effluent. Periodically during aeration, the exhaust flow was stopped for about 10 seconds while the gas sampling bottle was replaced with a clean bottle. The concentration of MB in the exhaust sample was determined by gas chromatography (GC). In these preliminary experiments, the load factor and pulp temperature were constant at 18% and 16° C. respectively, and the ventilation rate was varied from 400 l/h to 822 l/h. Plots were constructed of the natural log of the concentration of MB in the exhaust vs. elapsed time of aeration, and two-component decay curves were obtained. The points at which the slopes of the decay curve changed was determined using piecewise linear regression (Neter, Wasserman, and Kutner, *Applied Linear Statistical Models*, Second Edition, Richard D. Irwin, Inc., Homewood, Ill., pages 346-348 (1985)).

Subsequent experiments investigated the relationship between the rate of decline in the concentration of MB in the exhaust and in the apples with selected combinations of pulp temperatures, load factors, and ventilation rates. At intervals of 0.5, 1.0, 1.5, 2.0, 2.5, 3.5, 4.5, 6.5, 10.0, 22 hours after the beginning of aeration the exhaust flow was stopped for about 1.0 minute while a gas sampling bottle (125 ml) in the exhaust line was replaced with a clean bottle, the fumigation chamber was moved to a fume hood, and a sample of 4 to 6 apples were removed for residue determinations. The fumigation chamber then was returned to the environmental chamber and aeration continued. The residue concentration in the apples was determined by GC within 1.0 minute after sampling. The experiment was terminated after 22 hours and the apples were discarded.

Residue Determination. A rapid headspace analysis procedure was used for MB residue determinations (King et al., supra.) as follows: the apples were weighed into a 6 liter Waring blender flask, one liter of water was added, and the apples were blended for 1.5 minutes. The homogenate was allowed to stand for 1.0 minute, and a sample of the gaseous phase (headspace) injected into a GC.

Gas Chromatographic Conditions. Residues were determined with a Hewlett-Packard model 5840 GC equipped with a 1 ml gas sampling loop and an electron capture detector. The column was 1.85 meters×5 mm packed with Porapak Q (50-80 mesh) obtained from Waters Associates, Inc. The injector, column oven, and detector were operated at 200° C., 160° C., and 300° C. respectively, and the flow rate of the nitrogen carrier gas was 55 ml/min.

Quantification of Methyl Bromide in Residue and Exhaust Air. To prepare standards, 4 to 6 unfumigated whole apples were weighed, placed in a blender flask, and water was added as above. The flask was capped, MB diluted with air was injected into the headspace, and the contents were blended for 1.5 minutes. A sample of the headspace was then chromatographed. Usually 20 to 30 standards were prepared during each aeration period, and a regression equation based on concentration and peak area was used to calculate the residue concentration in fumigated apples. The limit of quantification was about 0.01 ppm, however, residues were not quantified below 0.2 ppm.

Standards for determining the concentration of MB in exhaust air were made by serial dilution of pure MB with air. A regression equation based on concentration and peak area was used to quantify MB in the exhaust samples. The limit of analysis was about 0.05 µg/l, but exhaust samples were not quantified below 1.0 µg/l. The detector response was linear within the range of quantification of the exhaust and residue standards.

Figure 3:
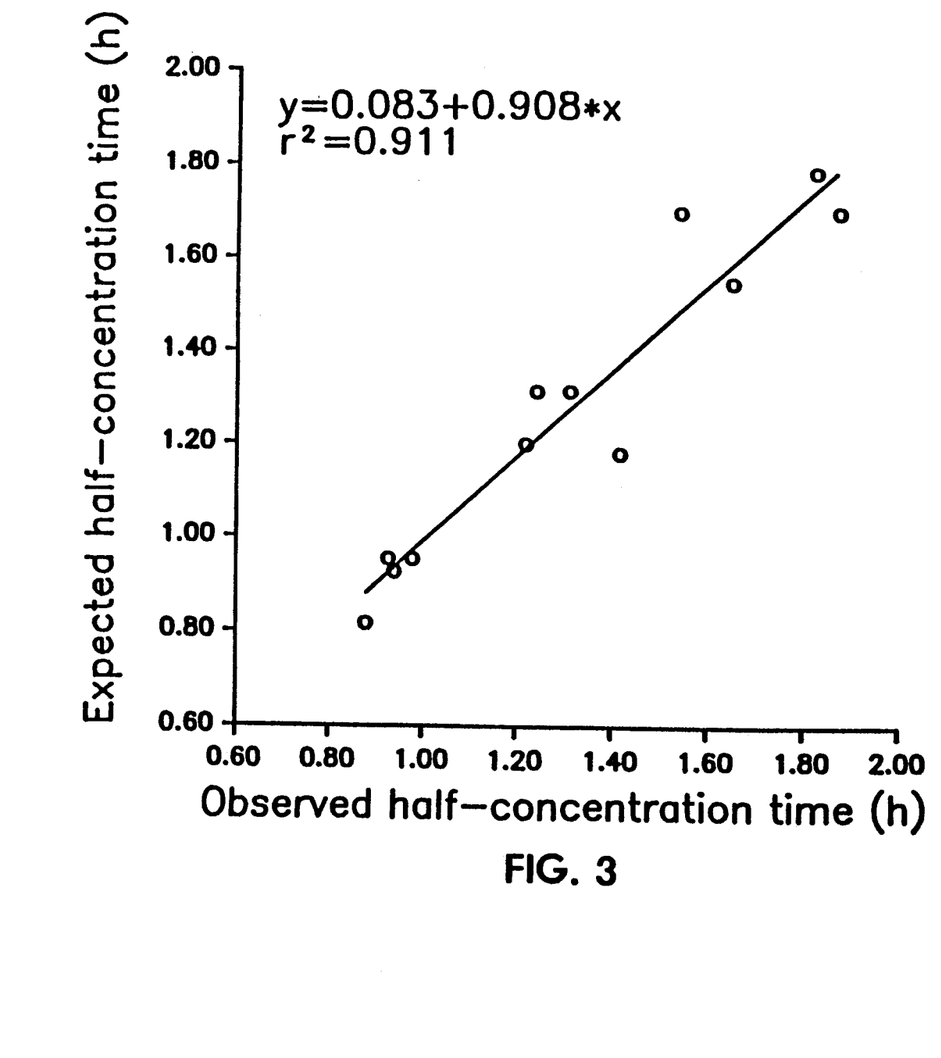
FIG. 3 shows the comparison between observed and expected half-concentration times for methyl bromide residue in apples. Observed half-concentration times were calculated from equation $t_{\frac{1}{2}} = (\ln 2)/k$ where ln 2 is the natural log of 2, k is the rate of desorption of MB from apples ($h^{-1}$). Expected half-concentration times were calculated from the equation $t_{\frac{1}{2}} = (\ln 2)/k^v$ where $k^v$ is the rate of decline of concentration of methyl bromide in exhaust air ($h^{-1}$).

Results. The experiments showed that the decline in concentration of MB in the exhaust air stream followed two consecutive first order decay curves (FIG. 2). As discussed above, the rate of the first decay curve depended on the velocity of the exhaust air stream and resulted primarily from removing gaseous MB from the free air space in the chamber, and the rate of the second decay ($k^v$) was shown to be independent of the velocity of the exhaust air stream and correlated well ($r^2=0.94$) with observed rate of desorption of MB from the commodity as determined by headspace analysis (Table I). The high correlation indicated that the determinations of MB in the exhaust could be used to obtain qualitative estimates of the persistence of MB in apples from calculations of the half-concentration times, which is the length of aeration required to reduce MB residue concentration by one-half. Estimated half-concentration times were in good agreement with observed half-concentration times (FIG. 3).

Also, a comparison is given (Table I) between the observed concentration of MB in the commodity at the beginning of aeration ($C_o$), as determined by headspace analysis, and as estimated from the y-intercept of the second decay curve ($C_o^v$). The correlation between the observed and estimated values ($r^2=0.63$) indicated that the method was sufficiently accurate over a wide range of fumigation conditions encompassed by these experiments.

Multiple regression was used on the data in Table I to determine the effects of load factor, pulp temperature, and ventilation rate on the estimated and observed regression statistics for the desorption of MB residue from apples (Table II). The coefficients for the multiple regression model overlapped at the 95% confidence level indicating that the expected and observed equations behaved essentially the same.

These results indicate that the equation:

$$C=(QC_o^v/Wk^v) \exp(-k^v t)$$

that is described above, can be used to accurately estimate the concentration of residual fumigant in commodities during the aeration period that follows fumigation. Assuming that a fumigated commodity must be aerated until the residual fumigant concentration reaches a designated concentration $C_t$, then the length of the aeration required to obtain this tolerance is obtained by rearrangement of the above prediction equation, giving:

$$t=(1/k^v) \ln (QC_o^v/Wk^v C_t).$$

As can be seen, determination of the MB concentration in the exhaust air stream can be used to estimate both the persistence and concentration of MB in apples during aeration. This technique is accurate over a wide range of fumigation conditions and is useful for estimating the length of the aeration period required to obtain the proposed tolerance of 0.2 ppm MB in apples.

TABLE I

| Fumigation parameters | | | | Regression statistics for the desorption of methyl bromide from thinning apples[b] | | |
|---|---|---|---|---|---|---|
| Pulp temp. (C.) | Load factor[a] (%) | Ventilation rate (l/h) | | Intercept $C_o$ or $QC_o^v/Wk^v$ (ppm) | Rate constant k or $k^v$ (l/h) | Coefficient of determination $r^2$ |
| 22 | 38 | 400 | observed[c] | 91.2 | 0.71 | 0.990 |
|  |  |  | estimated[d] | 92.1 | 0.73 | 0.996 |
| 22 | 38 | 822 | observed | 93.6 | 0.74 | 0.990 |
|  |  |  | estimated | 107.9 | 0.75 | 0.991 |
|  |  |  | Average = | 96.2 | 0.73 |  |
|  |  |  | SD = | 6.8 | 0.01 |  |
| 22 | 19 | 400 | observed | 135.5 | 0.79 | 0.990 |
|  |  |  | estimated | 111.2 | 0.85 | 0.983 |
| 22 | 19 | 822 | observed | 127.6 | 0.75 | 0.999 |
|  |  |  | estimated | 133.5 | 0.73 | 0.984 |
|  |  |  | Average = | 127.0 | 0.78 |  |
|  |  |  | SD = | 9.5 | 0.05 |  |
| 16 | 38 | 400 | observed | 99.6 | 0.56 | 0.996 |
|  |  |  | estimated | 100.5 | 0.53 | 0.990 |
| 16 | 38 | 584 | observed | 101.1 | 0.75 | 0.997 |
|  |  |  | estimated | 97.2 | 0.58 | 0.990 |
|  |  |  | Average = | 99.6 | 0.56 |  |
|  |  |  | SD = | 1.5 | 0.02 |  |
| 16 | 19 | 400 | observed | 134.7 | 0.53 | 0.995 |
|  |  |  | estimated | 143.9 | 0.53 | 0.984 |
| 16 | 19 | 584 | observed | 113.4 | 0.49 | 0.993 |
|  |  |  | estimated | 120.9 | 0.59 | 0.989 |
|  |  |  | Average = | 128.2 | 0.54 |  |
|  |  |  | SD = | 11.8 | 0.04 |  |
| 8 | 38 | 400 | observed | 100.8 | 0.37 | 0.998 |
|  |  |  | estimated | 117.5 | 0.41 | 0.994 |
| 8 | 38 | 752 | observed | 104.9 | 0.38 | 0.998 |
|  |  |  | estimated | 123.0 | 0.39 | 0.944 |
|  |  |  | Average = | 111.6 | 0.39 |  |
|  |  |  | SD = | 9.0 | 0.01 |  |
| 8 | 19 | 400 | observed | 134.9 | 0.42 | 0.999 |
|  |  |  | estimated | 169.7 | 0.45 | 0.990 |
| 8 | 19 | 752 | observed | 138.7 | 0.45 | 0.983 |
|  |  |  | estimated | 170.0 | 0.41 | 0.988 |
|  |  |  | Average = | 153.3 | 0.42 |  |
|  |  |  | SD = | 16.6 | 0.04 |  |

[a]Load factor is the ratio of volume of apples to volume of the fumigation chamber expressed as a percentage.
[b]Each observed and estimated regression curve was constructed with 10 residue or exhaust methyl bromide determinations.
[c]Observed regression statistics were derived from plots of ln C vs. t where ln C is the natural log of the concentration of methyl bromide residue in apples t (h) after the beginning of aeration. The slopes of the equations are k (l/h) and the antilog of the y-intercept is $C_o$ (ppm).
[d]Estimated regression statistics were calculated from plots of ln $C^v$ vs. t where ln $C^v$ is the natural log of the concentration (mg/l) of methyl bromide in the exhaust t (h) after the beginning of aeration. The slopes of these equations are $k^v$ (l/h) and the intercept is $QC_o^v/Wk^v$ (ppm), where Q is the ventilation rate (l/h) $C_o^v$ is the antilog of the y-intercept of the plot of ln $C^v$ vs. t and W is the mass of apples (kg).

TABLE II

| Desorption regression statistic[b] | Multiple regression model coefficients[a] | | | Coefficient of determination ($r^2$) |
|---|---|---|---|---|
|  | A | B | C |  |
| k | 0.20 | 0.024 | ne[c] | 0.913 |
|  | (0.11, 0.28) | (0.020, 0.029) |  |  |
| $k^v$ | 0.20 | 0.025 | ne | 0.910 |
|  | (0.11, 0.29) | (0.021, 0.030) |  |  |
| $C_o$ | 172.0 | −0.58 | −1.70 | 0.884 |
|  | (190.6, 153.4) | (0.20, −1.37) | (−1.23, −2.17) |  |
| $QC_o^v/Wk^v$ | 214.8 | −2.50 | −1.85 | 0.825 |
|  | (247.4, 182.3) | (−1.12, −3.86) | (−1.02, −2.68) |  |

[a]Multiple regression model of the form desorption rate or initial residue concentration = A + B (pulp temperature) + C (load factor). The 95% confidence interval is shown below each coefficient.
[b]See Table I.
[c]ne = no effect (i.e., p > .05).

EXAMPLE 2

The concentration of MB residue in fresh cherries was determined at different pulp temperatures and load factors. Comparison between observed (actual) half-concentration times for MB residue in cherries as determined by headspace analysis, and estimated half-concentration times is tabulated in Table III, below. Observed and estimated half-concentration times were determined as described above for FIG. 3. The data indicates that MB in exhaust gas samples can be used to predict residue concentration in cherries.

TABLE III

| Fumigation parameters | | Half-life of residue (hr) | |
|---|---|---|---|
| Pulp temp (°C.) | Load factor (%) | Actual | Estimated |
| 3.000 | 8.000 | 2.133 | 1.510 |
| 3.000 | 16.000 | 2.224 | 1.565 |
| 3.000 | 24.000 | 1.924 | 1.572 |
| 3.000 | 32.000 | 2.350 | 1.623 |
| 9.000 | 8.000 | 1.997 | 1.565 |
| 9.000 | 16.000 | 1.677 | 1.300 |
| 9.000 | 24.000 | 1.977 | 1.432 |
| 9.000 | 32.000 | 1.964 | 1.540 |
| 13.000 | 8.000 | 1.594 | 1.144 |
| 13.000 | 16.000 | 1.525 | 1.183 |
| 13.000 | 24.000 | 1.400 | 1.199 |
| 13.000 | 32.000 | 1.635 | 1.187 |
| 18.000 | 8.000 | 1.535 | 1.109 |
| 18.000 | 16.000 | 1.285 | 1.149 |
| 18.000 | 24.000 | 1.411 | 1.073 |
| 18.000 | 32.000 | 1.363 | 0.997 |
| 23.000 | 8.000 | 1.102 | 0.872 |
| 23.000 | 16.000 | 0.979 | 0.795 |
| 23.000 | 24.000 | 1.046 | 0.844 |
| 23.000 | 32.000 | 1.315 | 0.948 |

EXAMPLE 3

Walnuts (5.0 kg) were fumigated for 2 hours in a 28.3 liter fumigation chamber (described in Example 1) with 32 g/m$^3$ MB. After aeration began, samples of the exhaust air stream from the chamber were taken every 15 minutes and analyzed for MB using gas chromatography. As shown in FIG. 4, the results showed that the decline in the MB concentration in the exhaust air stream similar to that obtained for thinning apples (FIG. 2). The linearity of the second decay curve ($r^2 = 0.94$) indicates that the desorption of MB from walnuts follows first order kinetics and that the prediction equation can be used to estimate residue concentration in the walnuts.

EXAMPLE 4

A computer program for estimating residual fumigant in a commodity from the decline of concentration of fumigant in the exhaust air stream using the prediction equation is presented below. The program reads the signal from the fumigant analyzer at preselected intervals and performs a piecewise linear regression analysis on the 15 most-recently input data points to determine the point in time at which the second decay curve (second phase) begins. This is determined by noting the change in the correlation coefficient from strong to weaker to stronger values. At this point the residue estimation begins. The operator can change operating parameters (attenuation factor of the fumigant analyzer, sampling interval) at any time during the aeration process.

The program is designed to run on an Epson PX-8 Geneva portable computer and is specific to this computer due to its analog voltage input hardware. The code on lines 560 to 660 represent the machine language necessary to read the input signal. The rest of the program will work on any computer that uses a BASIC language compatible with Microsoft GW-BASIC.

First, a portion of memory is set aside for the machine language instruction for reading the input signal. These instructions are then read into this memory area in lines 100-110. The program waits for a key-press to begin sampling data, and records the the starting time in lines 130-150. Lines 170-200 sample the input signal at the selected interval and convert it to a concentration value with a calibration equation (specific to the fumigant analyzer being used). The point in time when the second decay curve occurs is found by processing the most recently acquired 15 data points by linear regression analysis, comparing successive correlation coefficients. The second decay curve occurs when the correlation coefficient changes from a higher value to a lower value, then back to a higher value. Once the start of the second curve is located, the input data are used to calculate the fumigant residue on the commodity using the prediction equation. These steps are performed in lines 300-420. Lines 220-290 are a subroutine which is called when the input signal is sampled. The signal is sampled four times and checked for abberations which are discarded if found. The average of the four readings are accumulated five times (lines 510-520). The value returned is the average of these twenty readings. Also, in this subroutine, lines 230-270 check for keyboard activity and perform the indicated operation. Line 340 extracts the hour, minute, and second form the current time of day reading.

It is understood that the foregoing detailed description is given merely by way of illustration and that modification and variations may be made within, without departing from the spirit and scope of the invention.

```
10  '
20  '
30  '           PROGRAM NAME: FUMICONC.BAS
40  '              FUNCTION: ESTIMATE FUMIGANT RESIDUE ON
50  '                        COMMODITIES USING A EPSON
60  '                        PX-8 LAPTOP COMPUTER.
70  '
80  DIM X(25),Y(25):CLS:M=PEEK(6)+PEEK(7)*256-100
90  CLEAR ,M
100 M=PEEK(6)+PEEK(7)*256-100:I=M
110 READ X:IF X>=0 THEN POKE I,X:I=I+1:GOTO 110
120 OPEN "O",1,"A:TEST.DAT":ET=0:CL$=SPACE$(40):ET9=60:AF=1:
    FL2CURV$="N":STRT$="N":PK$="N":R=-99:NPTS=15:PTR=1
130 CLS:INPUT"FLOW RATE";Q:INPUT"MASS OF COMMODITY";W:PRINT"GET
    READY TO TAKE READINGS AND THEN PRESS ANY KEY":PRINT
140 IF INKEY$="" THEN 140 ELSE CLS
150 GOSUB 510:GOSUB 540:EL=H*3600+M1*60+S:E2=E1:PRINT#1,
    H*10000+M1*100+S;0;X1
160 '
170 GOSUB 510:GOSUB 540:ET=H*3600+M1*60+S:IF ET-E2<ET9 THEN 170
180 E2=ET:E8=ET-E1:GOSUB 310
190 LOCATE 1,1:PRINT CL$:LOCATE 1,1:PRINT "TIME: ";X$;" CONCEN
    RATION = ";EXP(X1*.04451-6.9076);" (ET = ";
```

-continued

```
200  PRINT USING"####.## minutes)";E8/60:PRINT#1,H*10000+M1*
     100+S;E8;X1:GOTO 170
210  '
220  FOR I=1 TO 4:CALL M(Z%(I)):NEXT
230  A$=INKEY$:IF A$="" THEN 280 ELSE IF A$="S" OR A$="s" THEN
     260 ELSE IF A$="C" OR A$="c" THEN 250 ELSE IF A$="f" OR A$="F"
     THEN 270 ELSE LOCATE 1,6:PRINT"PAUSING - PRESS ANY KEY WHEN
     READY.";
240  IF INKEY$="" THEN 240 ELSE LOCATE 1,6:
     PRINT"              ":GOTO 280
250  LOCATE 1,6:INPUT"NEW SAMPLE INTERVAL (IN SECONDS)";ET9:
     LOCATE 1,6:PRINT"              ":GOTO
     280
260  LOCATE 1,6:INPUT"ARE YOU SURE (Y/N)";A$:IF A$="Y" OR A$="y"
     THEN CLOSE:END ELSE LOCATE 1,6:PRINT"              ":GOTO
     280
270  LOCATE 1,6:INPUT"ATTENUATION FACTOR";AF:LOCATE 1,6:
     PRINT"              "
280  IF ABS(Z%(1)-Z%(2))+ABS(Z%(3)-Z%(4))>3 THEN 220 ELSE X=(Z%
     (1)+Z%(2)+Z%(3)+Z%(4))/4
290  RETURN
300  '
310  RLAST=R:XT=E8/60:YT=X1*.04451-6.9076:IF FL2CURV$="Y" THEN
     340 ELSE X(PTR)=XT:Y(PTR)=YT:PTR=PTR+1
320  IF PTR>NPTS THEN PTR=1:STRT$="Y"
330  IF STRT$="N" THEN RETURN ELSE SUMX=0:SUMX2=0:SUMY=0:SUMY2=0:
     SUMXY=0:FOR I=1 TO NPTS:SUMX=SUMX+X(I):SUMX2=SUMX2+X(I)*X(I):
     SUMY=SUMY+Y(I):SUMY2=SUMY2+Y(I)*Y(I):SUMXY=SUMXY+X(I)*Y(I):NEXT
340  SUMX=SUMX+XT:SUMX2=SUMX2+XT*XT:SUMY=SUMY+YT:SUMY2=SUMY2+YT*YT:
     SUMXY=SUMXY+XT*YT:NPTS=NPTS+1
350  B=(NPTX*SUMXY-SUMX*SUMY)/(NPTS*SUMX2-SUMX*SUMX):A=(SUMY-B*
     SUMX)/NPTS:R=B*SQR((SUMX2-SUMX*SUMX/NPTS)/(SUMY2-SUMY*SUMY/NPTS))
360  IF FL2CURV$="Y" THEN PRINT USING"/   /
     ####.###";TIME$,Q*EXP(A)/W/B*EXP(-B*XT/60):RETURN
370  IF ABS(1-RLAST/R)<.001 THEN RETURN
380  IF R<=RLAST THEN 400 ELSE RMAX=R:IF PK$="Y" THEN PK$="N"
390  RETURN
400  IF PK$="N" THEN PK$="Y":ET8=0:RETURN
410  ET8=ET8+ET9:IF ET8<480 THEN RETURN
420  IF R<=.75*RMAX THEN FL2CURV$="Y":RETURN
500  '
510  X1=0:FOR I1=1 TO 5:GOSUB 220:X1=X1+X:NEXT:X1=X1/5*AF
520  LOCATE 1,5:PRINT TIME$:LOCATE 18,5:PRINT"    ":
     LOCATE 18,5:PRINT X1:RETURN
530  '
540  X$=TIME$:H=VAL(LEFT$(X$,2)):M1=VAL(MID$(X$,4,2)):S=VAL
     (RIGHT$(X$,2)):RETURN
550  '
560  DATA &H3E,&H2C       :' LD   A,2CH       ;SEND CODE TO READ ADC
570  DATA &HD3,6          :' OUT  (06),A
580  DATA &H3E,2          :' LD   A,2         ;WAIT FOR STATUS "DONE"
590  DATA &HD3,1          :' OUT  (01),A
600  DATA &HDB,5          :' IN   A,(05) {RDY}
610  DATA &HCB,&H5F       :' BIT  3,A
620  DATA &H28,&HFA       :' JR   Z,RDY
630  DATA &HDB,6          :' IN   A,(06)      ;READ DATA FROM
     SUBPROCESSOR
640  DATA &H77            :' LD   (HL),A      ;STORE AT ADDRESS OF
     PASSES VARIABLE
650  DATA &HC9            :' RET
660  DATA -1
```

Having thus described our invention, we claim:

1. A method for reducing residual fumigant to a desirable level in a commodity in a fumigation chamber having a free air space therein, comprising:

(a) determining the weight of said commodity in said chamber;

(b) passing a gas through said chamber in first and second phases to remove fumigant; wherein said free air space is depleted of fumigant and residual fumigant is released from said commodity during said first phase; wherein residual fumigant in said commodity is further released therefrom during said second phase; wherein said gas is passed through said chamber during said second phase at a known volumetric flow rate;

(c) determining the rate of decline of fumigant in gas exiting from said chamber during said second phase, so that there is a continual or intermittent update of the rate of decline;

(d) determining the concentration of fumigant in gas exiting from said chamber at the beginning of said first phase that is due to fumigant released from said commodity;

(e) continuing said second phase at least until said desirable level of residual fumigant in said commodity is reached as estimated from a predetermined relationship between:
(i) said weight,
(ii) said volumetric flow rate, (iii) said concentration of fumigant in exit gas at the beginning of said first phase that is due to fumigant released from said commodity;
(iv) the latest update of said rate of decline of fumigant in exit gas;
(v) the length of time between the beginning of said first phase and said latest update of the rate of decline.

2. The method of claim 1 wherein said predetermined relationship is in accordance with the following formula:

$$C=(QC_o^v/Wk^v) \exp(-k^v t)$$

wherein C is the concentration of residual fumigant in said commodity at time t after the beginning of said first phase; Q is said volumetric flow rate of the gas during said second phase; $C_o^v$ is said concentration of fumigant in exit gas at the beginning of said first phase that is due to fumigant released from said commodity; W is said weight of said commodity in said chamber, and $k^v$ is the rate of decline of fumigant in exit gas in said second phase.

3. A method for estimating the concentration of residual fumigant in a commodity which has been fumigated in a fumigation chamber having a free air space therein, which comprises:
   (a) determining the weight of said commodity in said chamber;
   (b) passing a gas through said chamber in first and second phases to remove fumigant; wherein said free air space is depleted of fumigant and residual fumigant is released from said commodity during said first phase; wherein residual fumigant in said commodity is further released therefrom during said second phase; wherein said gas is passed through said chamber during said second phase at a known volumetric flow rate;
   (c) determining the rate of decline of fumigant in gas exiting from said chamber during said second phase, so that there is a continual or intermittent update of the rate of decline;
   (d) determining the concentration of fumigant in gas exiting from said chamber at the beginning of said first phase that is due to fumigant released from said commodity; and
   (e) estimating the concentration of fumigant in the commodity using the prediction equation:

$$C=(QC_o^v/Wk^v) \exp(-k^v t)$$

wherein C is the concentration of residual fumigant in said commodity at time t after the beginning of said first phase; Q is said volumetric flow rate of the gas during said second phase; $C_o^v$ is said concentration of fumigant in exit gas at the beginning of said first phase that is due to fumigant released from said commodity; W is said weight of said commodity in said chamber, and $k^v$ is the rate of decline of fumigant in exit gas in said second phase.

4. A method for aerating a commodity for a time, t, to reach a desired tolerance of residual fumigant, $C_t$, in a commodity in a fumigation chamber having a free air space therein, which comprises:
   (a) determining the weight of said commodity in said chamber;
   (b) passing a gas through said chamber in first and second phases to remove fumigant; wherein said free air space is depleted of fumigant and residual fumigant is released from said commodity during said first phase; wherein residual fumigant in said commodity is further released therefrom during said second phase; wherein said gas is passed through said chamber during said second phase at a known volumetric flow rate;
   (c) determining the rate of decline of fumigant in gas exiting from said chamber during said second phase, so that there is a continual or intermittent update of the rate of decline;
   (d) determining the concentration of fumigant in gas exiting from said chamber at the beginning of said first phase that is due to fumigant released from said commodity;
   (e) continuing said second phase at least for a time, t, to reach a tolerance $C_t$ of residual fumigant in said commodity, wherein t is estimated in accordance with the following formula:

$$t=(1/k^v) \ln (QC_o^v/Wk^vC_t).$$

wherein t is the time to reach a desired tolerance concentration, $C_t$, of residual fumigant in said commodity; Q is said volumetric flow rate of the gas during said second phase; $C_o^v$ is said concentration of fumigant in exit gas at the beginning of said first phase that is due to fumigant released from said commodity; W is said weight of said commodity in said chamber, and $k^v$ is the rate of decline of fumigant in exit gas in said second phase.

5. A method for calculating a half-life, $t_{\frac{1}{2}}$, of residual fumigant in a commodity in a fumigation chamber having a free air space therein, which comprises:
   (a) passing a gas through said chamber in first and second phases to remove fumigant; wherein said free air space is depleted of fumigant and residual fumigant is released from said commodity during said first phase; wherein residual fumigant in said commodity is further released therefrom during said second phase; wherein said gas is passed through said chamber during said second phase at a known volumetric flow rate;
   (b) determining the rate of decline of fumigant in gas exiting from said chamber during said second phase, and
   (c) calculating $t_{\frac{1}{2}}$ using the formula:

$$t_{\frac{1}{2}}=(\ln 2)/k^v$$

where $t_{\frac{1}{2}}$ is the half-life, ln 2 is the natural log of 2, and $k^v$ is the rate of decline of said second phase.

6. An apparatus for estimating the concentration of residual fumigant in a commodity in a fumigation chamber having a free air space therein, including a fumigation chamber, means for passing a gas through the chamber in first and second phases to remove fumigant from a known weight of commodity; wherein the free air space is depleted of fumigant and residual fumigant is released from the commodity during the first phase; wherein fumigant in the commodity is further released therefrom during the second phase; wherein the gas is passed through the chamber at a known volumetric flow rate, wherein the improvement comprises:
   (a) means communicating with said chamber for sampling said gas exiting said chamber and for transferring said exit gas sample to a fumigant analyzer;
   (b) a fumigant analyzer communicating with said sampler means which produces a signal in response to concentration of fumigant in said exit gas sample to provide continuous or intermittent measurements of said concentration of fumigant in said exit gas sample, and (c) computing means operatively associated with said fumigant analyzer for processing said known weight, said known volumetric flow rate, and said fumigant concentration measurements (i) to determine the rate of decline of fumigant in said exit gas during said second phase, so that there is a continual or intermittent update of the rate of decline, (ii) to determine the concentration of fumigant in gas exiting from said chamber at the beginning of said phase that is due to fumigant released from said commodity, and (iii) to estimate the concentration of residual fumigant in said commodity from a predetermined relationship between:

(i) said known weight,
(ii) said known volumetric flow rate,
(iii) said concentration of fumigant in exit gas at the beginning of said first phase that is due to fumigant released from said commodity;
(iv) the latest update of said rate of decline of fumigant in exit gas;
(v) the length of time between the beginning of said first phase and said latest update of the rate of decline.

7. The apparatus of claim 6 wherein said predetermined relationship is in accordance with the following formula:

$$C = (QC_o^v / Wk^v) \exp(-k^v t)$$

wherein C is the concentration of residual fumigant in said commodity at time t after the beginning of said first phase; Q is said volumetric flow rate of the gas during said second phase; $C_o^v$ is said concentration of fumigant in exit gas at the beginning of said first phase that is due to fumigant released from said commodity; W is said weight of said commodity in said chamber, and $k^v$ is the rate of decline of fumigant in exit gas in said second phase.

8. The apparatus of claim 6 which further includes means responsive to said computing means for discontinuing passing said gas through said chamber when said estimated concentration of residual fumigant reaches a preset value.

* * * * *